(12) United States Patent
Chon et al.

(10) Patent No.: US 11,844,725 B2
(45) Date of Patent: Dec. 19, 2023

(54) VISUALLY TRACEABLE VITRECTOMY PROBE CAP

(71) Applicant: Alcon Inc., Fribourg (CH)

(72) Inventors: James Y. Chon, Irvine, CA (US);
Nathaniel Reyes, Santa Ana, CA (US);
John R. Underwood, Laguna Nigel, CA (US); Ravi Durvasula, Irvine, CA (US)

(73) Assignee: Alcon Inc., Fribourg (CH)

( * ) Notice: Subject to any disclaimer, the term of this patent is extended or adjusted under 35 U.S.C. 154(b) by 380 days.

(21) Appl. No.: 17/071,132

(22) Filed: Oct. 15, 2020

(65) Prior Publication Data
US 2021/0113379 A1    Apr. 22, 2021

Related U.S. Application Data

(60) Provisional application No. 62/915,698, filed on Oct. 16, 2019.

(51) Int. Cl.
*A61F 9/007* (2006.01)
*A61B 90/30* (2016.01)

(52) U.S. Cl.
CPC .......... *A61F 9/00763* (2013.01); *A61B 90/30* (2016.02); *A61B 2090/304* (2016.02)

(58) Field of Classification Search
CPC ...... A61F 9/00763; A61F 9/007; A61B 90/30; A61B 2090/304; A61B 17/320783; A61B 5/0059; A61B 2017/00486; A61B 2017/00477; A61B 1/00112; A61B 2050/0063; A61B 2050/008; A61B 2050/0084

See application file for complete search history.

(56) References Cited

U.S. PATENT DOCUMENTS

| | | |
|---|---|---|
| 3,764,796 A | 10/1973 | Gilliam et al. |
| 3,774,022 A | 11/1973 | Dubrow et al. |
| 3,819,925 A | 6/1974 | Richter et al. |
| 3,933,118 A | 1/1976 | Lyons et al. |
| 4,064,428 A | 12/1977 | Van Zandt |
| 4,651,753 A * | 3/1987 | Lifton .................... A61B 10/04 600/564 |
| 7,600,405 B2 | 10/2009 | Maurer, Jr. |
| 8,545,462 B2 | 10/2013 | Ghannoum |
| 8,968,347 B2 | 3/2015 | Mccollam |
| 8,979,867 B2 | 3/2015 | Peyman |
| 9,364,982 B2 | 6/2016 | Schaller |
| 10,307,290 B2 | 6/2019 | Kern |
| 2005/0065496 A1* | 3/2005 | Simon .................... A61M 1/84 604/500 |
| 2006/0229627 A1* | 10/2006 | Hunt .................... A61F 2/4465 606/86 R |
| 2008/0154292 A1* | 6/2008 | Huculak ............. A61F 9/00763 606/167 |

(Continued)

*Primary Examiner* — Jocelin C Tanner
(74) *Attorney, Agent, or Firm* — Patterson + Sheridan, LLP (57) ABSTRACT

A vitrectomy probe with a light emitting, visibly discrete traceable probe cap. The light emitting, visibly discrete character of the probe cap may aid a surgeon in tracing the end of a needle of the vitrectomy during a vitrectomy procedure. The probe cap may be of a biocompatible polymer accommodating phosphorescent pigment or of another suitable light source.

13 Claims, 6 Drawing Sheets

(56) References Cited

U.S. PATENT DOCUMENTS

| | | | | |
|---|---|---|---|---|
| 2011/0071391 | A1* | 3/2011 | Speeg | A61B 90/39 |
| | | | | 600/431 |
| 2016/0022489 | A1* | 1/2016 | Hartstra | A61F 9/00736 |
| | | | | 606/166 |
| 2016/0038155 | A1* | 2/2016 | Griffith | A61B 17/1322 |
| | | | | 606/203 |
| 2016/0244666 | A1* | 8/2016 | Lai | C09K 11/7792 |
| 2017/0014269 | A1* | 1/2017 | Draheim | A61F 9/00763 |
| 2019/0046288 | A1* | 2/2019 | Anderson | A61B 17/0231 |
| 2019/0201238 | A1 | 7/2019 | Bacher | |
| 2019/0239979 | A1 | 8/2019 | Abt | |
| 2022/0023096 | A1* | 1/2022 | Peterson | A61F 9/00763 |

\* cited by examiner

VISUALLY TRACEABLE VITRECTOMY PROBE CAP

PRIORITY CLAIM

This application claims the benefit of priority of U.S. Provisional Patent Application Ser. No. 62/915,698 titled "VISUALLY TRACEABLE VITRECTOMY PROBE CAP," filed on Oct. 16, 2019, whose inventors are Nathaniel Reyes, John R. Underwood, James Y. Chon and Ravi Durvasula, which is hereby incorporated by reference in its entirety as though fully and completely set forth herein.

BACKGROUND

Over the years, many dramatic advancements in the field of retinal eye surgery have taken place. However, regardless of the particular retinal procedure, it is common that a vitrectomy will be included in at least part of the procedure. Vitrectomy is the removal of some or all of the vitreous humor from a patient's eye. In some cases, where the surgery was limited to removal of clouded vitreous humor, the vitrectomy may constitute the majority of the procedure. However, a vitrectomy may also accompany cataract surgery, surgery to repair a retina, to address a macular pucker or a host of other issues.

The vitreous humor itself is a clear gel that may be removed by an elongated probe when inserted through a pre-placed cannula at the eye. More specifically, the probe includes a central channel for removal of the vitreous humor. Further, the cannula provides a structurally supportive conduit strategically located at an offset location at the front of the eye, such as the pars plana. In this way, the probe may be guidingly inserted into the eye in a manner that avoids damage to the patient's lens or cornea.

Of course, inserting a probe into a patient's eye doesn't just present injury concern at the front of the eye. Once the probe traverses structure at the front of the eye and continues forward, injury from an advancing probe to delicate structures near the back of the eye may be of concern. The issue is particularly of note given ever decreasing probe sizes. That is, to help minimize incision size at the front of the eye, the probe itself may be no more than 0.016 inches in diameter. While this is helpful in keeping the incision small enough that it will generally heal readily without substantial follow-on care, it also means that the probe is effectively a sharpened needle that is being advanced toward the delicate structures at the back of the eye as noted above. Thus, the risk to damage there may be increased. Considering that these structures include the retina, optic and other nerve tissue, needle-like damage thereto could result in localized near permanent eye impairment.

Efforts to minimize such probe damage at the rear of the eye have been undertaken. For example, vitrectomy probes are often manufactured with the add-on of a blunt end cap. The probe and the cap may be of suitably biocompatible treated metal with the cap being seam-welded onto the open end of the tubular probe. In this way, should the probe reach the delicate nerve tissue at the back of the eye, the encounter will be blunt and less like a knife or needle reaching the delicate tissue. That said, seam welding such a low profile component may be a challenging and somewhat expensive undertaking.

While making the probe cap blunt may be a good idea, avoiding such an encounter altogether would, of course, be more ideal. Unfortunately, ascertaining the precise location of the probe end can also be a challenge. That is, a metal probe end disposed within opaque vitreous humor may be difficult for a surgeon to consistently see even in the best of lighting conditions. Recall that the lighting here at issue is lighting within the limited confines of an eye. Thus, obtaining a precise and discrete visual contrast between the probe end and adjacent vitreous humor or other eye structure remains elusive. As a practical matter, enhancements that have improved incision recovery at the front of the eye have indirectly led to an increased risk to potentially permanent nerve damage at the rear of the eye.

SUMMARY

A vitrectomy probe is disclosed. The probe includes a needle with a port for the uptake of vitreous humor from an eye. The probe is outfitted with a substantially blunt end cap adjacent the port. Further, the cap comprises a light emitting component to enhance discrete visual tracking thereof.

DETAILED DESCRIPTION

In the following description, numerous details are set forth to provide an understanding of the present disclosure. However, it will be understood by those skilled in the art that the embodiments described may be practiced without these particular details. Further, numerous variations or modifications may be employed which remain contemplated by the embodiments as specifically described.

Embodiments are described with reference to certain types of vitrectomy probe surgical procedures. In particular, a procedure in which vitreous humor is removed to address vitreous hemorrhage is illustrated. However, tools and techniques detailed herein may be employed in a variety of other manners. For example, embodiments of a vitrectomy probe as detailed herein may be utilized to address retinal detachments, macular pucker, macular holes, vitreous floaters, diabetic retinopathy or a variety of other eye conditions. Regardless, so long as the vitrectomy probe incorporates a light emitting, visibly discrete traceable probe cap, appreciable benefit may be realized.

Figure 1:
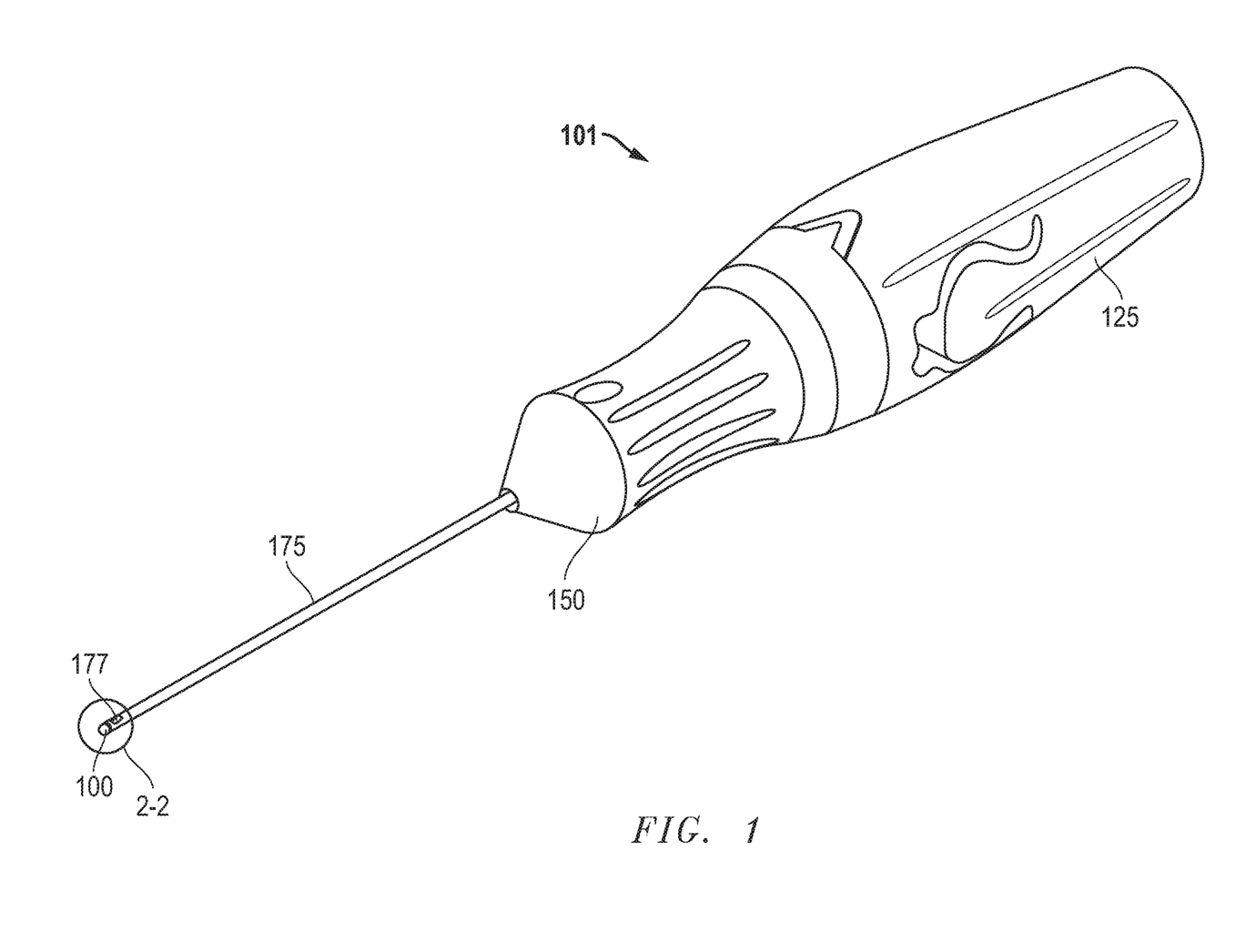
FIG. 1 is a perspective view of a vitrectomy probe employing an embodiment of a visibly discrete traceable probe cap.
Figure 4:
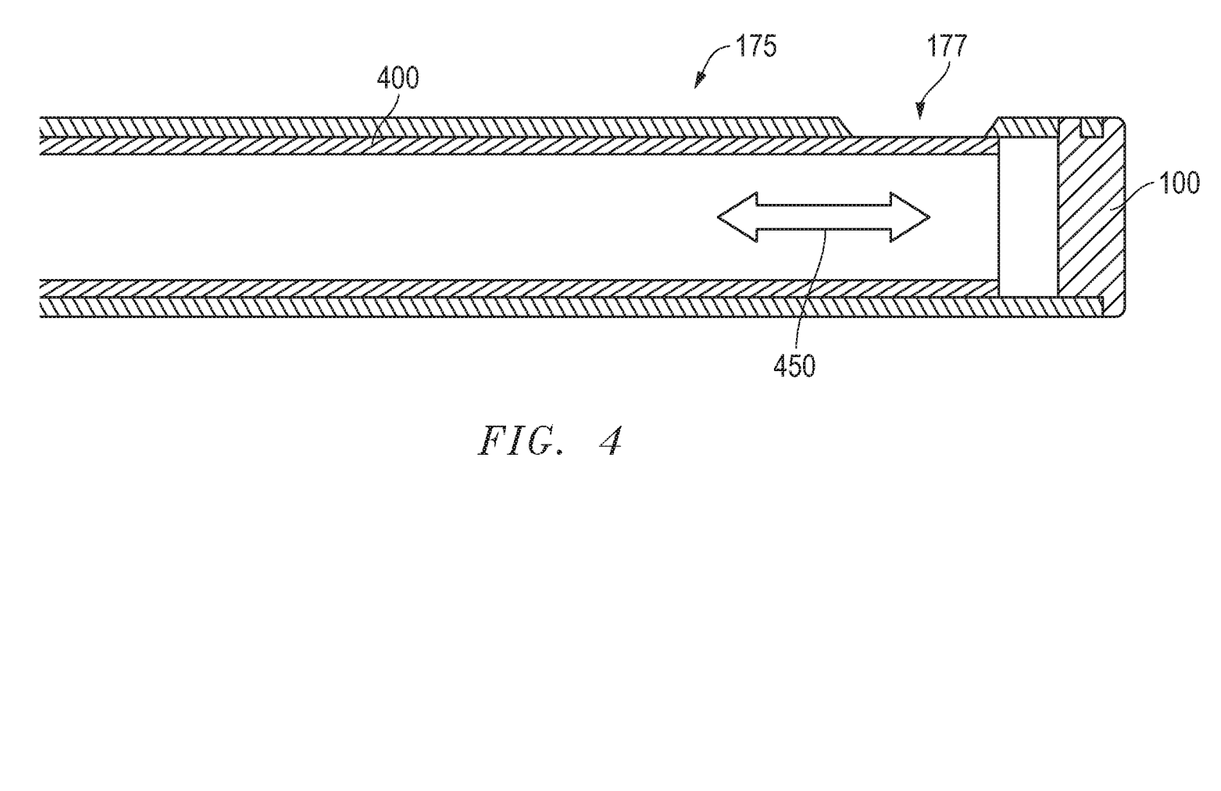
FIG. 4 is a side cross-section view of the probe needle of FIGS. 3A-3B upon incorporation of a cutter for a vitrectomy procedure.
Figure 5:
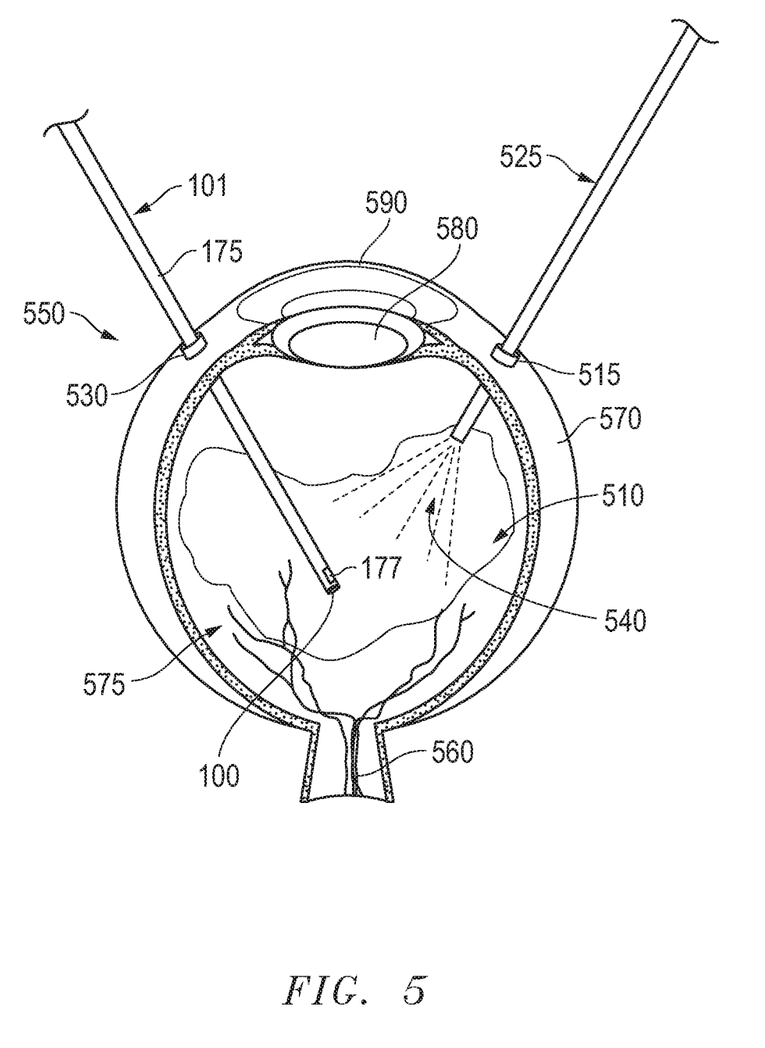
FIG. 5 is a side cross-sectional overview of a patient's eye during a vitrectomy procedure in which the vitrectomy probe of FIG. 4 is utilized.

Referring now to FIG. 1, a perspective view of a vitrectomy probe 101 is shown employing an embodiment of a visibly discrete traceable probe cap 100 at the end of a needle 175. In various embodiments, an outer diameter of the probe cap 100 may be approximately the same as an outer diameter of an end of the needle so that the probe cap does not result in the probe 101 having a larger overall gauge size. In some embodiments, sides of the probe cap 100 may be flush with an outer surface of the needle. In some embodiments, the probe cap may fit inside an end of the needle such that sides of the probe cap 100 are flush with an interior surface of the needle. In other embodiments, the probe cap may fit over an end of the needle (which may result in a larger overall gauge size for the needle). The probe 101 also includes a component housing 150 and a shell 125. During a vitrectomy procedure as illustrated in FIG. 5, the shell 125 may or may not be removed by the surgeon, depending on preference. Meanwhile the housing 150 accommodates a variety of components for reciprocating a cutter 400 as illustrated in FIG. 4 to facilitate the safe uptake of vitreous humor through the illustrated port 177.

Of course, continuing with added reference to FIG. 5, performing this type of procedure poses some degree of risk to the optic nerve 560, retina 575 and other more delicate features at the back of the eye 550. Thus, enhancing visible clarity for the surgeon as to the location of the end of the needle 175 may be of substantial benefit. Therefore embodiments detailed herein include a cap 100 for the needle 175 that is not only blunt but also includes a light emitting component. For example, the cap 100 may be comprised of a conventional polycarbonate material with phosphorescent pigment mixed therein. Both the polycarbonate and pigment would be conventional biocompatible materials. In one embodiment, the pigment selected is based on strontium oxide aluminate chemistry.

One advantage of utilizing phosphorescence to supply the light emitting component is the resulting "glow" or "glow-in-the-dark" nature supplied to the cap 100 as a result. That is, recall that the advantage here to the surgeon and patient is that the cap 100 be a visibly discrete and traceable probe cap 100. This is not a circumstance where high intensity light is necessarily advantageous. Indeed, too high a level of brightness might compromise the surgeon's ability to visibly and discretely identify the precise location of the cap 100. However, where a glow-in-the-dark, fluorescent, chemiluminescent or other suitably softer light emitting component is employed in the relatively dim environment of a patient's eye 550, the more precisely traceable the cap 100. Along these lines, the light emitting component may be no brighter than about 20,000 mcd/m$^2$ (millicandela per square meter), as a measure of luminescence. Indeed for some embodiments, a maximum of about 5,000 mcd/m$^2$ may be used.

In some embodiments, the color of the cap 100 may be selected to convey information about the vitrectomy probe (e.g., instrument tip gauge size). In some embodiments, the cap 100 may be orange to indicate 23 gauge, blue or teal to indicate 25 gauge, and purple to indicate 27 gauge. Other color selections are also contemplated.

Of course, a variety of different types of light sources may be utilized for the light emitting component, even sealably isolated LED (light emitting diode) electrical packages, for example. Additionally, in some embodiments, illuminating adjacent eye structure such as delicate features at the back of the eye 550 may be accomplished (see FIG. 5). In some embodiments, a visibly discrete traceable probe cap 100 may be used in addition to or in place of other lighting types (e.g., electrical). In some embodiments, the cap 100 and/or the entire probe 101 of FIG. 1 may be disposable following the surgery depicted in FIG. 5.

Figure 2A:
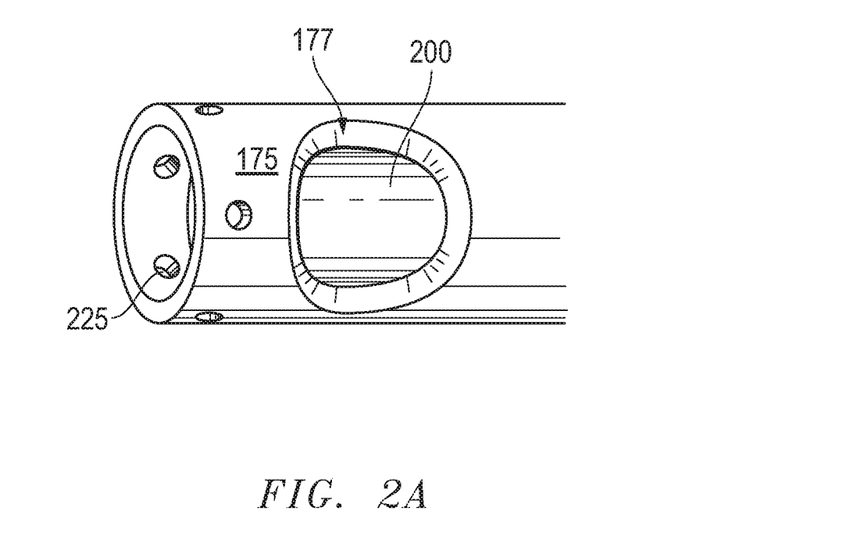
FIG. 2A is a side perspective view of a probe needle of the vitrectomy probe of FIG. 1 in advance of probe cap placement.
Figure 2B:
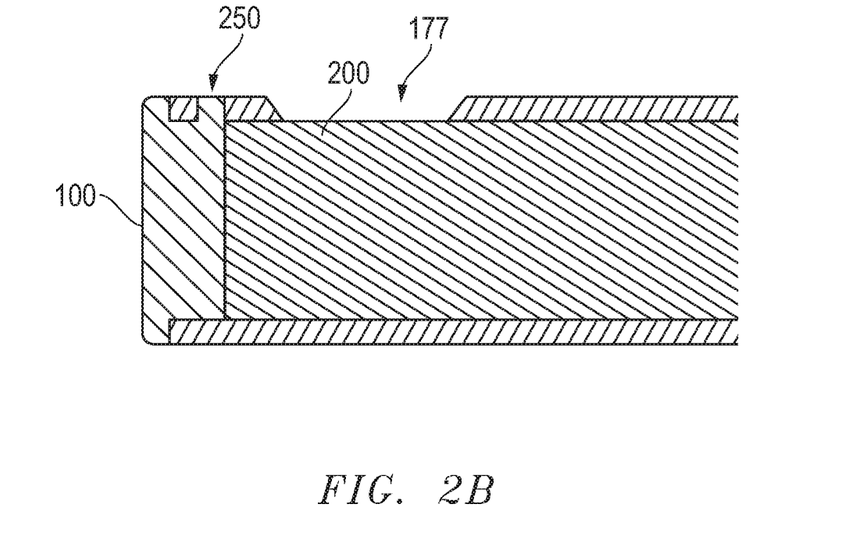
FIG. 2B is a side view of the probe needle of FIG. 2A with the addition of the probe cap of FIG. 1.

Referring now to FIG. 2A, a side perspective view of a probe needle 175 of the vitrectomy probe 101 of FIG. 1 is shown in advance of probe cap placement (as illustrated in FIG. 2B). In the view of FIG. 2A, the needle 175 is shown uncapped with a flat end that is perhaps no more than 0.016 inches in diameter and having orifices 225 circumferentially located thereabout. As discussed below, following over-molding, these orifices 225 will accommodate cap projections 250 that will help to keep the cap 100 in place as shown in FIG. 2B.

Continuing with reference to FIG. 2A, looking through the port 177 reveals a rod insert 200 that has been placed through the interior of the needle 175. In this way, the tip of the needle 175 may be exposed to over-molding with a suitable polymeric cap material as described above in order to form the cap 100 as illustrated in FIG. 2B.

Referring specifically now to FIG. 2B, a side view of the probe needle 175 of FIG. 2A is shown with the addition of the probe cap 100 of FIG. 1 following over-molding as discussed above. In this cross-sectional view, the rod insert 200 is more visible within the needle 175 to help define the molded cap 100. Similarly, the cap projections 250 are visible through the orifices 225 of FIG. 2A, permanently securing the cap 100 in place. Once set, the rod insert 200 may be removed, the cap 100 or projections 250 filed or otherwise surface treated if need be and the needle 175 is now ready for assembly with the remainder of the probe 101 of FIG. 1.

In some embodiments, the cap may be pre-formed and snapped into place on the end of the probe (e.g., pre-formed with one or more protrusions that fit into the orifices 225 as the cap is snapped into place). In some embodiments, an adhesive may be used to bond the cap to the end of the probe. The adhesive may be used with the protrusions or in place of (i.e., on a smooth cap interior) to hold the cap on the end of the probe.

Figure 3A:
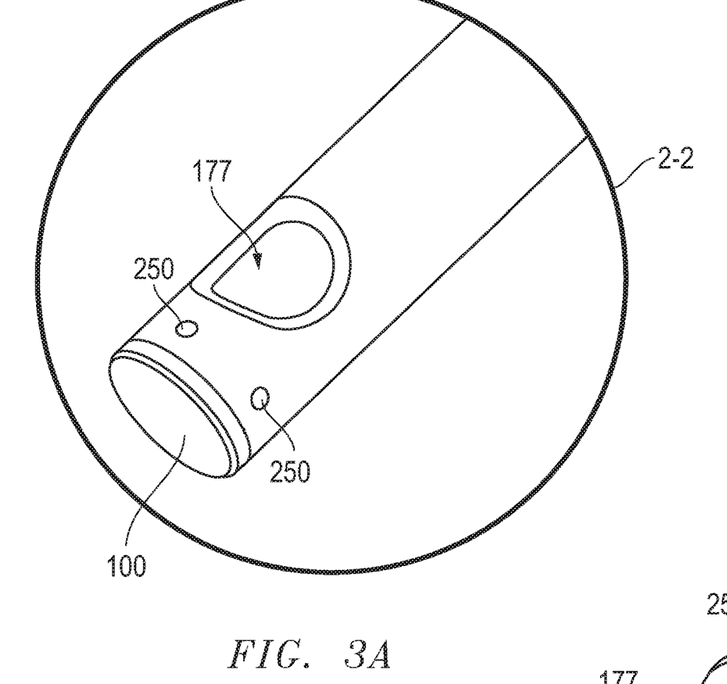
FIG. 3A is a first perspective view of an end of the assembled probe needle of FIG. 2A.
Figure 3B:
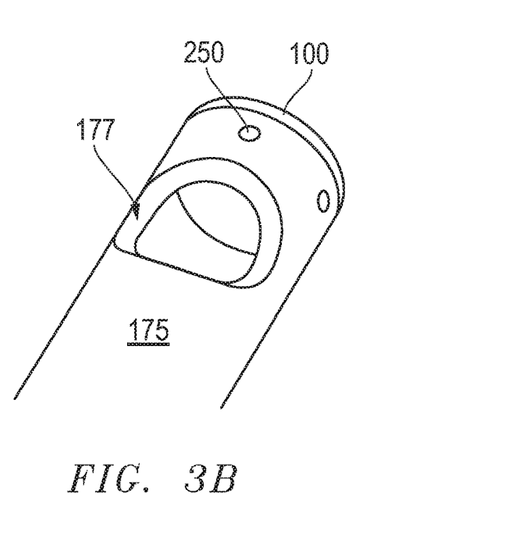
FIG. 3B is a second perspective view of the end of the assembled probe needle of FIG. 3A viewed from the opposite perspective.
Figure 3C:
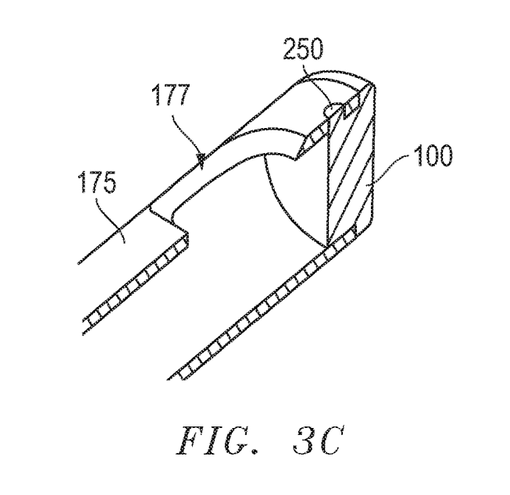
FIG. 3C is a perspective cross-sectional view of the end of the assembled probe needle, viewed from the perspective of FIG. 3B.

Referring now to FIGS. 3A-3C, different perspective views of the end of the assembled probe needle 175 are shown. Specifically, FIGS. 3A and 3B show first and second perspective views of the end of the needle 175 from opposite perspectives whereas FIG. 3C depicts a view similar to 3B but in a cross section. In these views, it is apparent that the post-overmolded fitted cap 100 at the end of the needle 175 is securely in place. Surface treated, polished or otherwise fashioned for biomedical use, the cap 100 appears tightly secured with projections 250 emerging from orifices 225 in the needle 175 (see FIG. 2A). As suggested above, the needle 175 is ready for incorporation into the remainder of the probe 101 as illustrated in FIG. 1.

Referring now to FIG. 4, a side cross-section view of the probe needle 175 of FIGS. 3A-3B is shown upon incorporation of a cutter 400 for a vitrectomy procedure. Specifically, as suggested above, the cutter 400 may be reciprocated at the interior of the needle 175. At the same time, vitreous humor of the eye 550 may be drawn in through a port 177. Reciprocating the cutter 400 as the vitreous humor is drawn in, chops up the vitreous humor so as to prevent the fibrous nature of the material from unintentionally pulling on eye structures as it is drawn into the needle 175.

In addition to the cutter function, the needle 175 now also includes another feature to help prevent undue eye damage during a vitrectomy procedure as illustrated in FIG. 5. Specifically, the addition of a visibly discrete traceable probe cap 100 as detailed above also helps to avoid undue eye damage during the procedure. That is, not only does the probe cap 100 provide a polymeric blunt end to an otherwise sharp end needle 175, but it is now readily and precisely visible to the surgeon due to the particular light emitting characteristics described herein.

Referring now to FIG. 5, a side cross-sectional overview of a patient's eye during a vitrectomy procedure is shown. In this view, the vitrectomy probe 101 of FIG. 1, with the cutter 400 of FIG. 4, is utilized. During this surgical procedure, the needle 175 is inserted through a preplaced cannula 530 and directed toward a region 510 where vitreous humor is to be removed. Specifically, as described above, a suction is applied and the port 177 is used for the uptake of the vitreous humor or other substances. For example, in the procedure illustrated, a hemorrhage may be taking place in the region 510 such that blood is drawn into the port 177 along with the vitreous humor.

As also described above, a cutter 400 is reciprocating within the needle 175 during this delicate procedure (see FIG. 4). This means that a diaphragm within the housing 150 of FIG. 1 is repeatedly reciprocating the cutter 400 of FIG. 4, likely in excess of 10,000 times per minute. The surgery illustrated includes the probe 101 and a light instrument 525 reaching into the eye 550 through cannulas 515, 530 positioned in an offset manner at the sclera 570. In this way, the more delicate cornea 590 and lens 580 may be avoided. By the same token, the optic nerve 560 and retina 575 are also quite delicate. Therefore, given that the needle 175 is capable of reaching these delicate features, it may illuminate both the back of the eye 550 and the end of the needle 175 for the surgeon.

In one embodiment, the cap 100 may be exposed to intense light for a period of time sufficient to activate phosphorescent pigment thereof. Thus, as the probe 101 and needle 175 are advanced, a visibly discrete traceable character may be provided to the end of the probe that is prone to encounter delicate eye features. By the same token, illuminating the delicate eye features may be achieved with the light instrument 525. In the embodiment shown, incandescent light 540 may be provided by way of the light instrument 525. This light 540 may have a degree of intensity that is greater than that emitted by the cap 100. This is because the instrument 525 may be kept away from more delicate eye features, being utilized to illuminate such features from a distance. The cap 100 on the other hand may need to reach closer to such delicate features during operation. Thus, with these features already illuminated, employing the light emitting character of the cap 100 for tracing its location within the murky confines of the eye 550 may be of substantial benefit.

Figure 6:
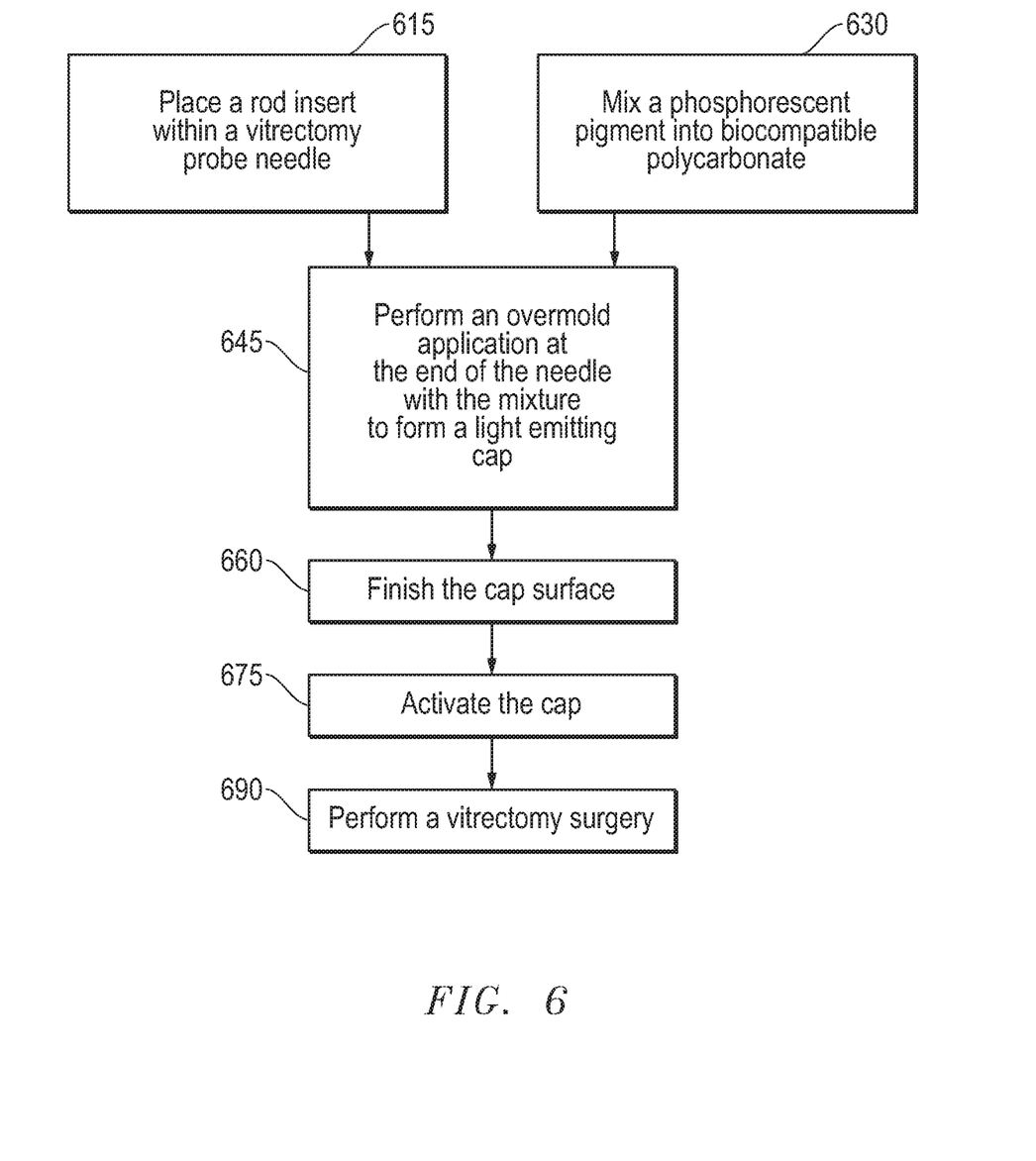
FIG. 6 is a flow-chart summarizing an embodiment of assembling and employing a vitrectomy probe with a visibly discrete traceable probe cap.

Referring now to FIG. 6, a flow-chart summarizing an embodiment of assembling and employing a vitrectomy probe with a visibly discrete traceable probe cap is shown. As indicated at 615, a probe needle may be provided with a rod insert positioned within the needle as a specific location. At the same time, a polymeric mixture that will constitute the cap to be formed may be mixed (see 630). Specifically, a biocompatible polycarbonate may have phosphorescent pigment mixed there-into. Although other material choices and/or light emitting types may be utilized as well. Regardless, as indicated at 645, where a mold-type of cap is to be formed, it may be overmolded at the end of the needle to form the light emitting cap. It is worth noting that this not only provides the added benefits described herein but also presents a less challenging and less expensive manner of capping the needle, in contrast to, for example, seam welding a metal blunt end. Further, the cap itself may be finished at the surface and the needle assembled into the remainder of the probe (see 660).

Of course, when ready for surgery, where such a glow-in-the-dark embodiment is utilized, activation with a high degree of light exposure may take place as indicated at 675. Indeed, depending on the duration of the surgery, re-activation by another high intensity light exposure to the cap may be undertaken. For example, the light 540 of the instrument 525 may be utilized to attain such a recharge during a surgical procedure. In either case, the activated light emitting cap is ready to provide a visibly discrete and traceable character to the end of the needle for the vitrectomy (see 690).

Embodiments described hereinabove include a probe cap that is both blunt and light emitting. Once more, the type of light emitted is tailored to providing a visible discrete and traceable character to the end of the needle. Thus, avoiding damage to sensitive eye features may be better avoided during a vitrectomy procedure. In this manner, a beneficial aid is provided to both surgeon and patient alike. Furthermore, in contrast to a metal blunt end, a polymeric probe cap may provide a less harsh point of contact should delicate eye features come into contact with the cap.

The preceding description has been presented with reference to various embodiments. However, other embodiments and/or features of the embodiments disclosed but not detailed hereinabove may be employed. Furthermore, persons skilled in the art and technology to which these embodiments pertain will appreciate that still other alterations and changes in the described structures and methods of operation may be practiced without meaningfully departing from the principle and scope of these embodiments. Additionally, the foregoing description should not be read as pertaining only to the precise structures described and shown in the accompanying drawings, but rather should be read as consistent with and as support for the following claims, which are to have their fullest and fairest scope.

We claim:

1. A vitrectomy probe, comprising:
   a needle with a port for uptake of vitreous humor from an eye; and
   a light emitting, visibly discrete traceable probe cap adjacent the port at an end of the needle, wherein:
   the cap comprises a plurality of cap projections extending radially outward from the cap;
   the needle comprises a plurality of orifices positioned circumferentially around the end of the needle, the plurality of orifices extending between an external surface of the needle and an internal surface of the needle, the plurality of orifices configured to receive the plurality of cap projections for fixedly coupling the cap to the needle; and
   the plurality of cap projections comprises outer surfaces that are flush with an outer surface of the needle.

2. The vitrectomy probe of claim 1, wherein the cap comprises a biocompatible polymer with a phosphorescent pigment mixed therein.

3. The vitrectomy probe of claim 2, wherein the light is less than about 20,000 mcd/m$^2$ (millicandela per square meter) as a measure of luminescence.

4. The vitrectomy probe of claim 1, further comprising a cutter located in the needle for cutting the vitreous humor during the uptake.

5. The vitrectomy probe of claim 4, further comprising a housing with cutter reciprocating components therein to facilitate reciprocating of the cutter for the cutting.

6. The vitrectomy probe of claim 1, wherein the probe cap is bonded to the end of the needle via an adhesive.

7. The vitrectomy probe of claim 1 wherein a color of the probe cap indicates a gauge size of the vitrectomy probe.

8. A needle for a vitrectomy probe, the needle comprising:
   a light emitting, visibly discrete traceable probe cap defining an end of the needle for advancing into an eye of a patient, wherein:
   the cap comprises a plurality of cap projections extending radially outward from the cap;
   the needle comprises a plurality of orifices positioned circumferentially around the end of the needle, the plurality of orifices extending between an external surface of the needle and an internal surface of the needle, the plurality of orifices configured to receive the plurality of cap projections for fixedly coupling the cap to the needle; and
   the plurality of cap projections comprises outer surfaces that are flush with an outer surface of the needle.

9. The needle of claim 1, wherein an outer diameter of the probe cap is approximately the same as an outer diameter of the end of the needle.

10. The needle of claim 8, wherein the light is one of fluorescent, chemiluminescent and glow-in-the-dark light.

11. The needle of claim 10, wherein the light is the glow-in-the-dark light and the probe comprises a polycarbonate phosphorescent pigment mix.

12. The needle of claim 8, wherein the probe cap is bonded to the end of the needle via an adhesive.

13. The needle of claim 8, wherein a color of the probe cap indicates a gauge size of the vitrectomy probe.

\* \* \* \* \*